(12) United States Patent
Jacobsen et al.

(10) Patent No.: US 10,533,709 B2
(45) Date of Patent: Jan. 14, 2020

(54) GAS CYLINDER CONTROL SYSTEM AND GAS CYLINDER FOR USE THEREWITH SYSTEM

(71) Applicant: Linde Aktiengesellschaft, München (DE)

(72) Inventors: Brian Jacobsen, Horsham (GB); Mandip Thind, Southall (GB); Raj Gupta, Liversedge (GB); Rigoberto Perez de Alejo, Farnham (GB); Piers Lambert, Camberley (GB)

(73) Assignee: Linde Aktiengesellschaft, München (DE)

( * ) Notice: Subject to any disclaimer, the term of this patent is extended or adjusted under 35 U.S.C. 154(b) by 105 days.

(21) Appl. No.: 15/562,611

(22) PCT Filed: Mar. 17, 2016

(86) PCT No.: PCT/EP2016/055861
§ 371 (c)(1),
(2) Date: Sep. 28, 2017

(87) PCT Pub. No.: WO2016/156059
PCT Pub. Date: Oct. 6, 2016

(65) Prior Publication Data
US 2018/0112827 A1    Apr. 26, 2018

(30) Foreign Application Priority Data

Apr. 1, 2015 (GB) .................................. 1505671.6

(51) Int. Cl.
*F17C 13/00* (2006.01)
*F17C 13/02* (2006.01)
(Continued)

(52) U.S. Cl.
CPC ......... *F17C 13/003* (2013.01); *A61M 16/201* (2014.02); *F17C 13/02* (2013.01);
(Continued)

(58) Field of Classification Search
None
See application file for complete search history.

(56) References Cited

U.S. PATENT DOCUMENTS

| 4,223,692 A | 9/1980 | Perry |
| 2003/0189492 A1 | 10/2003 | Harvie |

(Continued)

OTHER PUBLICATIONS

International Search Report for PCT/EP2016/055861, dated Jun. 1, 2016, Authorized Officer: Michail Papagiannis, 2 pages.
(Continued)

*Primary Examiner* — Carlos R Ortiz Rodriguez
(74) *Attorney, Agent, or Firm* — Harness Dickey & Pierce P.L.C.

(57) ABSTRACT

The present invention provides a control system (10) for managing the supply of bottled gas to users (12), the system comprising: a gas cylinder system (14) having a gas cylinder (15) for receiving and distributing gas contained therein; a first electronic monitoring system (16) associated with said gas cylinder system (14) and operable to monitor parameters associated with said cylinder system (14); a second monitoring system (18) associated with one or more locations (A-F) in which said cylinder may reside and being operable to monitor the presence or absence of said cylinder within said one or more locations (A-F); and a computer system (20) in communication with each of said second monitors (18) for receiving information therefrom relating to the presence or absence of said cylinder system (14) in said one or more locations (A-F).

23 Claims, 3 Drawing Sheets (51) Int. Cl.
*A61M 16/20* (2006.01)
*A61B 5/0205* (2006.01)
*A61B 5/021* (2006.01)
*A61B 5/024* (2006.01)
*A61B 5/08* (2006.01)
*A61B 5/083* (2006.01)
*A61B 5/117* (2016.01)
*A61B 5/145* (2006.01)
*G05D 7/06* (2006.01)

(52) U.S. Cl.
CPC ............... *A61B 5/021* (2013.01); *A61B 5/024* (2013.01); *A61B 5/0205* (2013.01); *A61B 5/0816* (2013.01); *A61B 5/0833* (2013.01); *A61B 5/117* (2013.01); *A61B 5/14542* (2013.01); *A61B 2503/00* (2013.01); *F17C 2201/0104* (2013.01); *F17C 2201/032* (2013.01); *F17C 2205/0326* (2013.01); *F17C 2205/0394* (2013.01); *F17C 2205/05* (2013.01); *F17C 2221/011* (2013.01); *F17C 2221/017* (2013.01); *F17C 2223/0123* (2013.01); *F17C 2250/032* (2013.01); *F17C 2250/034* (2013.01); *F17C 2250/036* (2013.01); *F17C 2250/043* (2013.01); *F17C 2250/0417* (2013.01); *F17C 2250/0426* (2013.01); *F17C 2250/0439* (2013.01); *F17C 2250/0473* (2013.01); *F17C 2250/0478* (2013.01); *F17C 2260/015* (2013.01); *F17C 2270/025* (2013.01); *F17C 2270/0745* (2013.01); *G05D 7/0635* (2013.01)

(56) References Cited

U.S. PATENT DOCUMENTS

| | | | |
|---|---|---|---|
| 2005/0056090 A1* | 3/2005 | McSheffrey, Jr. | A62C 37/50 73/291 |
| 2007/0157734 A1 | 7/2007 | Skwara | |
| 2009/0040049 A1 | 2/2009 | Delecourt et al. | |
| 2010/0131213 A1 | 5/2010 | Bleys et al. | |
| 2011/0140850 A1 | 6/2011 | Wassel et al. | |
| 2011/0247620 A1* | 10/2011 | Armstrong | B01D 53/047 128/204.23 |
| 2012/0188076 A1 | 7/2012 | McSheffrey | |
| 2014/0224029 A1 | 8/2014 | McSheffrey et al. | |
| 2015/0316521 A1* | 11/2015 | Goldman | A23B 7/148 73/31.05 |

OTHER PUBLICATIONS

Great Britain Search and Examination Report for GB Appl. No. GB1505671.6, dated Sep. 30, 2015, 8 pages.

* cited by examiner

FIG. 1

GAS CYLINDER CONTROL SYSTEM AND GAS CYLINDER FOR USE THEREWITH SYSTEM

The present invention relates to a gas cylinder control system and a gas cylinder system for use therewith and relates particularly, but not exclusively, to such control systems and cylinder systems for supplying clinical gasses such as, for example, oxygen, nitrous oxide, Xenon, nitric oxide, helium and mixtures thereof to patients.

Presently, it is known to supply cylinder systems into a process including filling, transporting, storing and using before having the cylinder systems returned to the supplier for re-filling and then re-circulation within the process. The tracking of cylinder systems and the management of gas supply whilst at locations within the system is problematic as it is sometimes difficult to monitor the location of cylinder systems and how much gas is present in each cylinder being used. It is also known to supply cylinder systems with gauges displaying the pressure of gas remaining but human intervention is required in order to retrieve the information and some users may find it difficult to interpret the information supplied and may make incorrect determinations of total time of gas supply remaining etc. Still further, it is very difficult to locate cylinder systems which may be past their use-by date or which may be obsolete or inappropriate for a particular location.

It is also known to provide alarm systems associated with the supply of gas to patients but, generally, such alarm systems require the intervention of medical staff or particular skills so as to ensure correct evaluation and control.

It is, therefore, an object of the present invention to provide an improved control system for controlling the supply of gas from a source thereof and an improved cylinder system for use with said control system. Elements of the control system of the present invention may be applied to a wall mounted gas supply but they are preferably and most usefully applied to a gas cylinder based gas supply system referred to herein as a cylinder system as it will include components in addition to just a gas cylinder.

The present invention will be described in relation to the delivery of oxygen to a patient but may be applied to the delivery of other gasses to a patient or to another end user.

According to a first aspect of the present invention, there is provided a system for managing the supply of bottled gas to users, the system comprising: a gas cylinder system having a cylinder for receiving and distributing gas contained therein; a first electronic monitoring system associated with said gas cylinder and operable to monitor parameters associated with said cylinder; a second monitoring system associated with one or more locations in which said cylinder may reside and being operable to monitor the presence or absence of said cylinder within said one or more locations; and a computer system in communication with each of said second monitors for receiving information therefrom relating to the presence or absence of said cylinder in said one or more locations.

Preferably, said first monitoring system is configured for monitoring one or more of cylinder specific data (CSD) relating to any one or more of: cylinder identification (ID), gas supply time remaining, expiry date, cylinder type, cylinder location, environmental temperature, gas usage, time since filling, rate of gas usage, internal cylinder gas pressure, internal cylinder gas temperature, usage data, transportation data, gas remaining.

Advantageously, the system includes a patient monitor for monitoring patient specific data (PSD) configured to monitor one or more of the following patient specific data (PSD): patient identity, patient type, blood pressure, heart rate, oxygen saturation, breathing and gas usage and wherein said patient monitor is connected to said first monitoring system for transmitting patient specific data (PSD) to said first monitoring system.

Advantageously, the system may also include an environment monitor for monitoring environment specific data (ESD) configured to monitor one or more of the following environment specific data (ESD): location, smoke, temperature, movement or vibration. The system may also include a GPS location device associated with said cylinder for broadcasting the geographical location of said cylinder.

In a preferred arrangement, said first electronic monitoring system includes a transmitter for transmitting data to said second monitoring system, a further device or a human interface module.

Advantageously, said second monitoring system also includes a transmitter for transmitting data to said computer system, a further device or a human interface module.

Preferably, said first electronic monitoring system includes a receiver for receiving information or commands from said second monitoring system, a further device or a human interface module.

Advantageously, said second electronic monitoring system also includes a receiver for receiving information or commands from said computer system, a further device or a human interface module.

Preferably, said computer includes a management system for receiving monitored data (MD). The management system may include a command module for causing operational commands to be transmitted to said first monitoring system dependent upon monitored data (MD) received thereby.

The cylinder system may include a controllable outlet valve for controlling the gas output from said cylinder system and wherein said first monitoring system includes a controller, said outlet valve is operably linked to said controller for being controlled thereby and wherein said valve is controllable to alter or prevent the flow of gas from said cylinder system dependent upon commands received from said second monitoring system, said further device or a human interface module.

Advantageously, the system is programmed with one or more automatic valve closure commands (AVCC) for being transmitted to said first monitoring system upon receipt of an adverse situation signal (AS) generated by detection of any one or more of: smoke, adverse vibration, adverse movement, adverse temperature, excessive or non-programmed gas usage, excessive or unexpected gas pressure, gas dispensing in the absence of receipt of patient specific data (PSD), passage of an expiry date, unexpected or non-programmed location of cylinder system, absence of a command signal from said computer system, a further device or a human interface module.

In one arrangement, the system may include an automatic check and restart function (ACRF) for periodically checking received data after valve closure due to detection of an adverse situation signal (AS) and re-starting gas flow in the absence of receipt of a further adverse situation signal (ASS). The automatic check and restart function (ACRE) may include an intelligent restart function (IRF) for allowing gas to be delivered in accordance with a pre-determined control strategy.

Preferably, said first monitoring system includes an operable mode (OM) in which it is fully operational and a sleep mode (SM) in which it is not fully operable but is able to be placed back into the operable mode upon receipt of a signal from said second monitoring system and wherein said second monitoring system is operable to send a signal to said first monitoring system to cause said first monitoring system to adopt said operable mode (OM) or said sleep mode (SM) as and when required.

Conveniently, the system may include a human interface module for providing information or warnings to a user or accepting cylinder operational command inputs from a user and wherein said human interface module has multiple modes of operation and wherein said first monitoring system is operable to alter the mode of operation of the interface module dependent upon an inputted signal from said second monitoring system. The human interface module may be operable to change or cancel any one or more of: audio output, visual output, operational command output, user access capability, user interface capability, operational capability. The human interface module may also be operable to receive patient specific data (PSD) including patient identification, patient type information.

The system may include a wireless communication system between said first monitoring system and said second monitoring system and may include a wireless communication system between said second monitoring system and said computer system.

The computer system may comprises a cloud based computer system or a mainframe computer system.

Preferably, there is provided a memory (101) for storing any one or more of patient specific data (PSD), cylinder specific data (CSD), and environment specific data (ESD).

The present invention will now be more specifically described by way of example only with reference to the accompanying drawings, in which.

Figure 1:
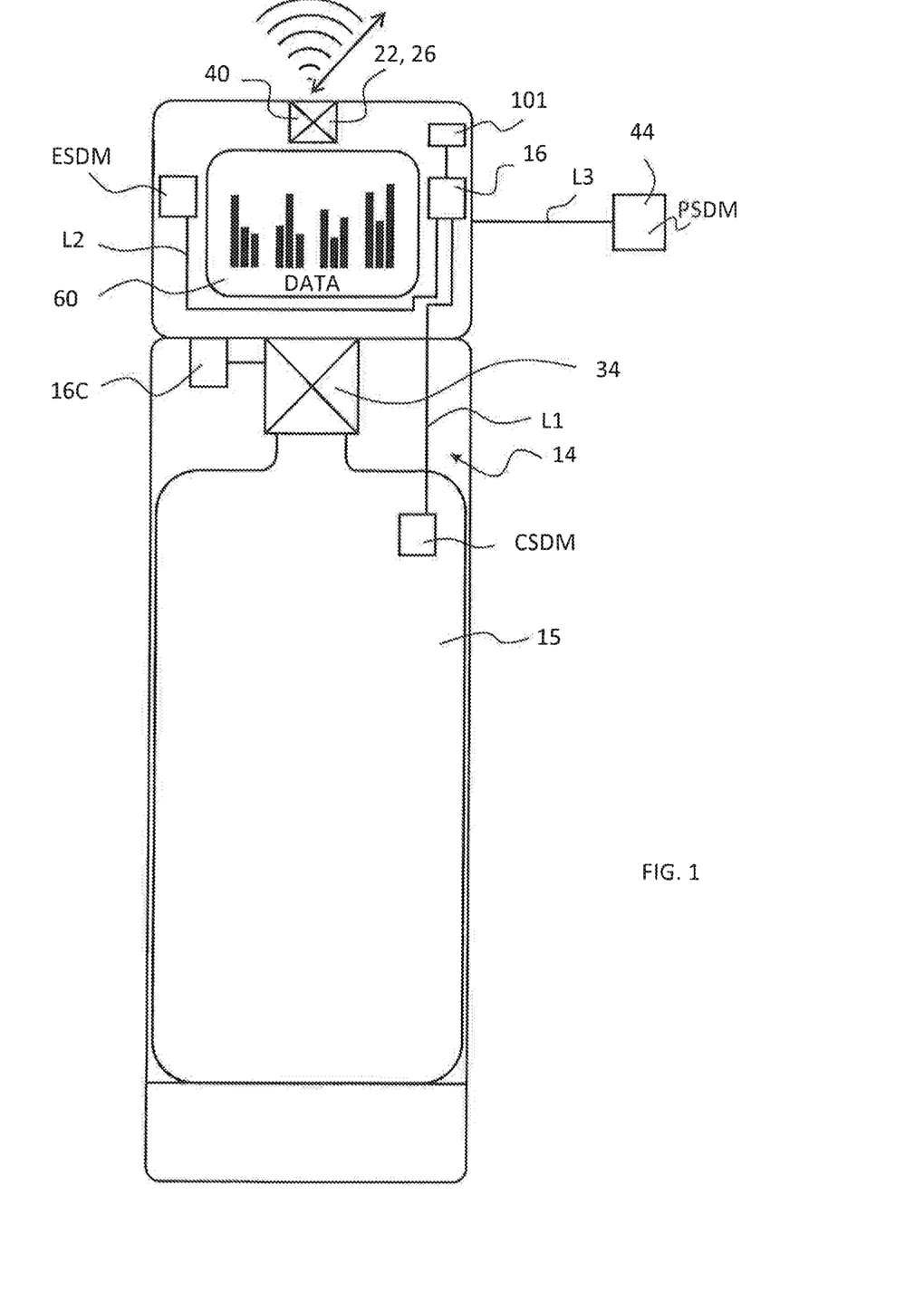
FIG. 1 is a general view of a cylinder in accordance with an aspect of the present invention.
Figure 2:
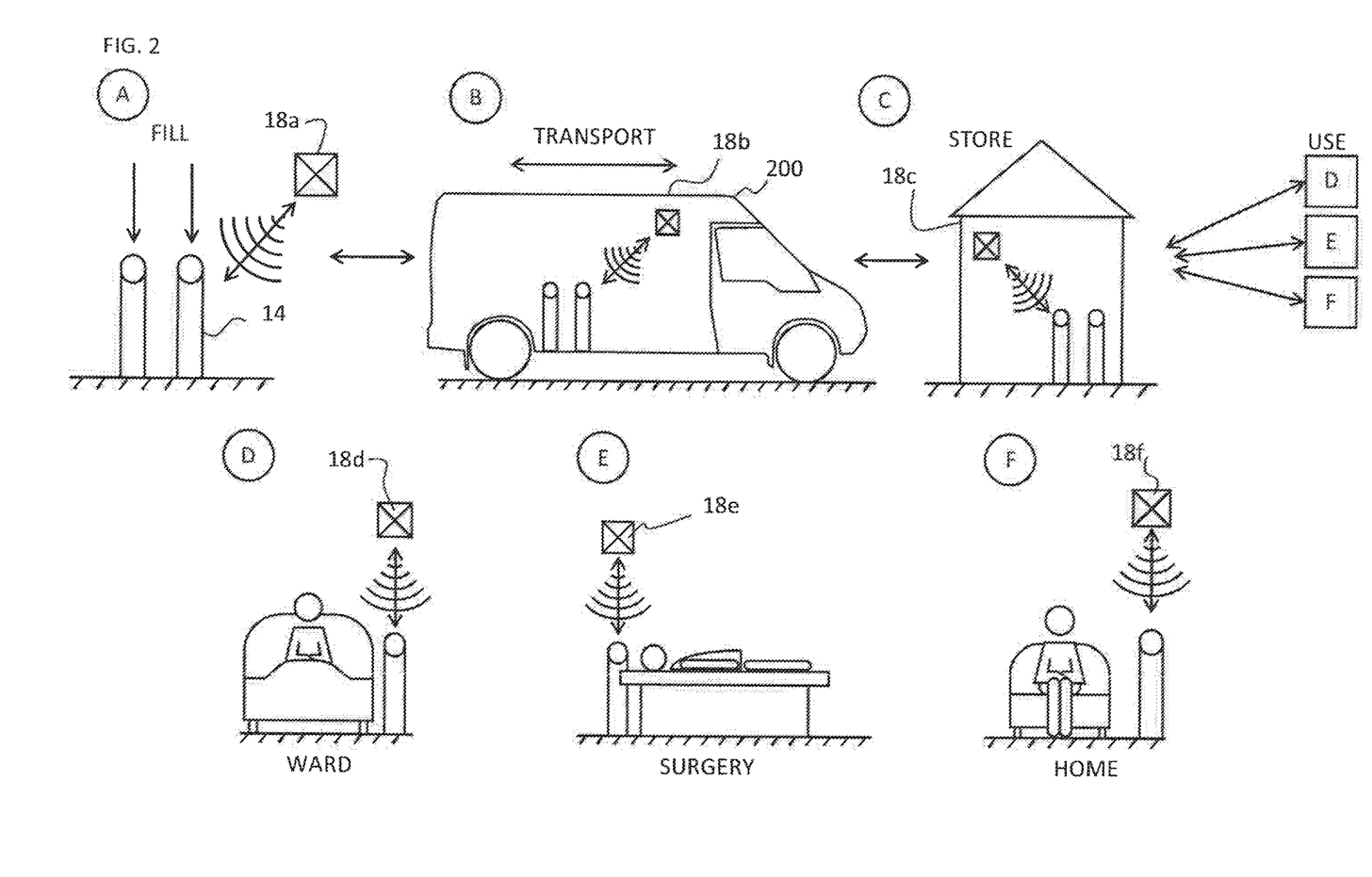
FIG. 2 is an overview of the system according to an aspect of the present invention.

Referring now to the drawings in general but particularly to FIG. 1, it will be appreciated that a cylinder system (14) may be located in any one of a number of locations during its lifecycle and that it is often difficult simply to locate a cylinder that is known to be in the supply chain. The typical supply chain includes a number of locations including but not limited to a filling station (A), a transportation vehicle (B), a storage facility (C) and any one of a number of use locations such as those shown at D to F. such use locations may include: a hospital ward (D), surgery, (E) or home (F). The cylinder system (14) of the present invention includes a first monitoring system (16) for monitoring cylinder specific data (CSD) or patient specific data (PSD) as discussed in detail later herein. The provision of the first monitoring system is significant as it is this which is used by the system of FIGS. 1 and 2 to improve the gas management from the cylinder system itself. The first monitor is provided with a transmitter (22) for transmitting data to a further device and may also be provided with a receiver (26) for receiving data or command signals from a further device. Each of these further devices are discussed in detail later herein. One or more of the locations (A-F) are provided with second monitoring system (18) which is operable to transmit and/or receive data and/or command signals via transmitter (24) and/or receiver (26). Preferably, each and every location (A-F) is provided with a second monitoring system (18). Preferably, the second monitors (18) are each operable to monitor at least the location of any cylinder system (14) provided with a first monitoring system (16) but they may be operable as described later herein to monitor more data and/or initiate commands/transmit received data to a further device. The further device may be any one or more of a server or computer system (20), a further device (60) or a human interface system (70), each of which is described in more detail later herein. The further device (60) and or human interface system (70) may be provided with a software application (app) to facilitate human interaction including display of information and modification or control through human input.

Referring now more particularly to FIG. 1 for a while, the cylinder system (14) may also be provided with a cylinder specific data monitor (CSDM) for monitoring cylinder specific data (CSD) such as, for example: cylinder identification (ID), gas supply time remaining, expiry date, cylinder type, cylinder location, environmental temperature, gas usage, time since filling, rate of gas usage, internal cylinder gas pressure, internal cylinder gas temperature, usage data, transportation data, gas remaining. The cylinder may also include an environment specific data monitor (ESDM) for monitoring environment specific data (ESD) and/or a patient specific data monitor (PSDM) (44) for monitoring patient specific data (PSD). The environment specific data may include any one or more of: location, smoke, temperature, movement or vibration, whilst the patient specific data may include any one or more of: oxygen saturation, patient identity, patient type, blood pressure, heart rate, breathing and gas usage. Each of the monitors is operably connected via lines (L1-L3) to the first monitoring system (16) for transmitting said data thereto. The cylinder system (14) may also include a global positioning system (GPS) and transmitter (GPS), a wireless transmitter (WT) or any such similar devices for broadcasting its location, as shown generally at (40).

The cylinder system (14) further includes a controllable outlet valve (34) for controlling the gas output from said cylinder (15) and the first monitoring system (16) includes a controller (16c) operably linked to said outlet valve (34), wherein said valve (34) is controllable to alter or prevent the flow of gas from said cylinder system (14) dependent upon commands received. Such commands may be transmitted to said first monitoring system (16) by the second monitoring system (18), a further device (60) or a human interface (70). In one arrangement the first monitoring system (16) may also be programmed to respond to one or more automatic valve closure commands (AVCC) transmitted thereto upon receipt of an adverse situation signal (AS) generated by detection of any one or more of: smoke, adverse vibration, adverse movement, adverse temperature, excessive or non-programmed gas usage, excessive or unexpected gas pressure, gas dispensing in the absence of receipt of patient specific data (PSD), passage of an expiry date, unexpected or non-programmed location of cylinder system (14), absence of a command signal from said second monitoring system (18), a further device (60) or a human interface module (70). The system may also include an automatic check and restart function (ACRF) for periodically checking received data after valve closure due to detection of an adverse situation signal (AS) and re-starting gas flow in the absence of receipt of a further adverse situation signal (ASS). Said system may include an automatic check and restart function (ACRF) includes an intelligent restart function (IRF) for allowing gas to be delivered in accordance with a pre-determined control strategy. These functions may be provided in the first monitoring system (16), the second monitoring system (18) or a further device such as a server or computer (20) as discussed later herein. The said first monitoring system (16) may include an operable mode (OM) in which it is fully operational and a sleep mode (SM) in which it is not fully operable but is able to be placed back into the operable mode upon receipt of a signal from said second monitoring system (18). Said second monitoring system (18) is preferably operable to send a signal to said first monitoring system (16) to cause said first monitoring system (16) to adopt said operable mode (OM) or said sleep mode (SM) as and when required. However, it will be appreciated such a signal may be sent from any other suitably functional device. Such suitable other devices include a human interface module (70) for providing information or warnings to a user or accepting cylinder operational command inputs from a user. Preferably, said human interface module (70) has multiple modes of operation and wherein said first monitoring system (16) is operable to alter the mode of operation of the interface module (70) dependent upon an inputted signal from said second monitoring system (18). Such an imputed signal may comprise a location signal which, upon receipt by the first monitoring system causes the triggering of a change of state of one or other or both of the valve position and/or the status of the human interface module (70). The valve position may be altered such as to prevent or allow or restrict or control gas delivery when said cylinder is in a particular location or absent from a location with a second monitoring system. The human interface may be altered such as to: enable or disable audio alarms; mute such alarms; enable or disable visual alarms; reduce light output from such alarms. Any audio or visual alarms or displays may be provided separately to other portions of the interface (70) and may comprise discrete alarms or displays positioned at convenient locations on the cylinder system (14) or in close proximity thereto. Said human interface module (70) may be operable to change or cancel any one or more of: audio output, visual output, operational command output, user access capability, user interface capability or operational capability. Said human interface module (70) may also be operable to receive patient specific data (PSD) and for displaying same to a member of hospital staff, the patient or another person. The system (10) may also include a memory (101) for retrievably storing any one or more of patient specific data (PSD), cylinder specific data (CSD) and environment specific data (ESD). This memory may be accessible by the human interface (70) such as to allow hospital staff to view patient specific data such as to make treatment decisions based thereon. Such an arrangement is of particular use when the memory (101) is incorporated in association with the cylinder system (14) such that it moves with the cylinder. This will allow hospital staff to quickly and easily read the patient specific data of an incoming or new patient and integrate that data into any patient management or any patient treatment programme. The memory may also be operably linked to the first monitoring system (16) such as to allow it to be accessible by the second monitoring system (18). The second monitoring system (18) may also be operable to transmit any one or more of patient specific data (PSD), cylinder specific data (CSD) or environment specific data (ESD) to a further device (60), the human interface (70) or the computer system (20) for subsequent analysis thereon by any one of a number of members of staff who have access to the further device or the human interface (70).

The further device (60) mentioned above may be mounted on the cylinder itself or may be a freestanding computer (62) having a display (64), a hand-held computer device (66), a mobile telephone (68) or any such similar device. Such devices are easily integrated into the system (10) and their use would allow data such as patient specific data to be more easily shared between those who need it. Such sharing of data will, inevitably, improve patient care.

Communication between any of the devices (16), (18), (20), (60), (70) may be by means of wired connections W or wireless connections WL. The further device (60) and/or human interface system (70) may be provided with a software application (app) to facilitate human interaction including display of information and modification or control through human input.

Figure 3:
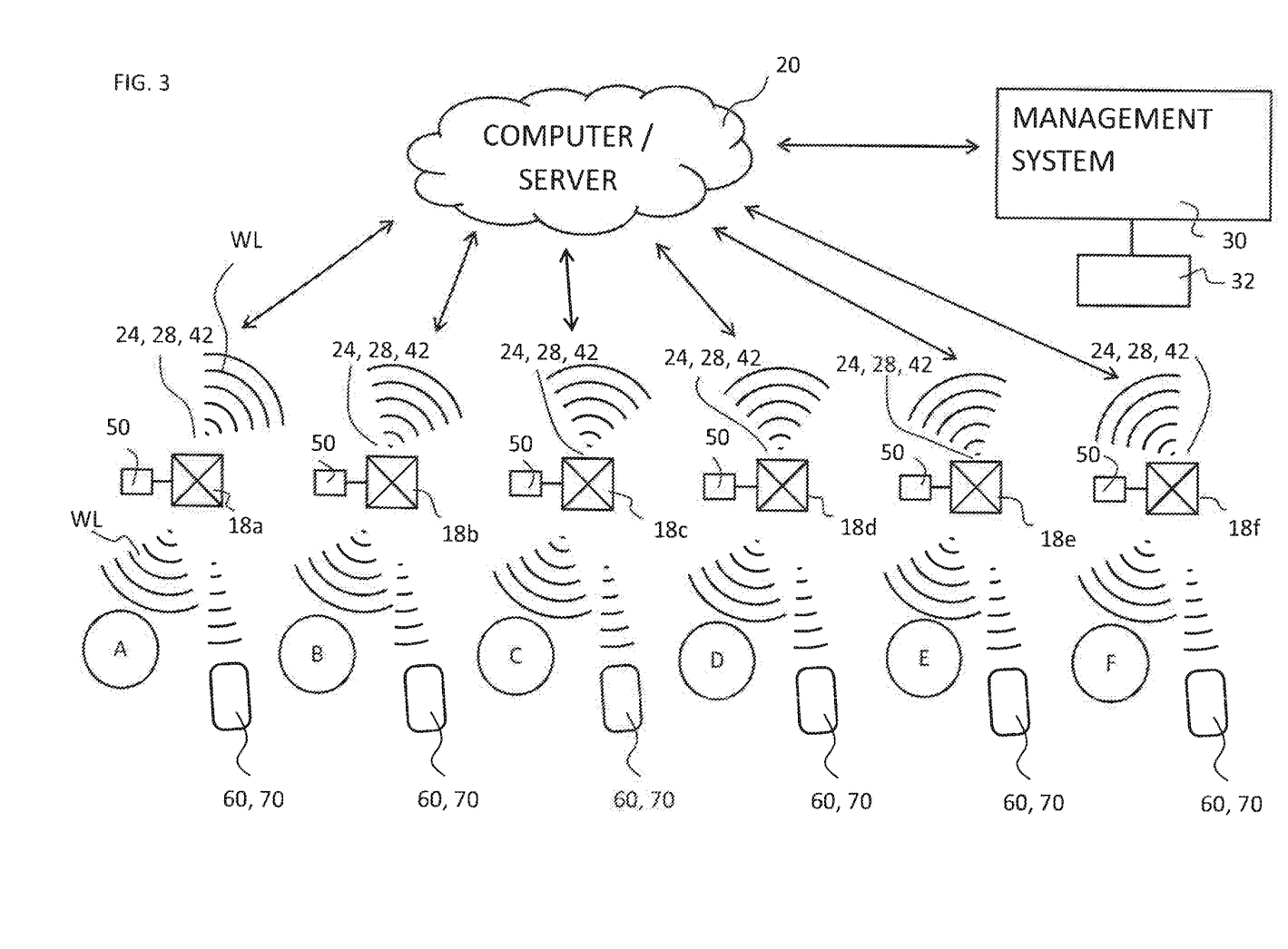
FIG. 3 is a detailed view of one portion of the system shown in FIG. 2.

Referring now more particularly to FIG. 3, the system (10) may further include a computer system (20) for receiving any one or more of the patient specific data (PSD), cylinder specific data (CSD) and/or environment specific data (ESD). Such a computer (20) may be a mainframe computer in a hospital to a cloud based server. Either arrangement of computer (20) may be operably connected to a management system (30) for allowing management of the cylinder systems (14) or system (10) as and when desired. Such a system (30) may further include an input device such as a keyboard (32) or screen or may be linked to a further device (60) or human interface module (70). Typical management activities may include: controlling certain types of cylinders such that they are not able to dispense gas in certain locations or when outside of certain locations; restricting or stopping the supply of gas from cylinders during certain times; emergency shut-down of cylinders in the event of fire or other dangerous situations; initiating audio or visual alarms on cylinders; communicating with hospital staff or patients through the human interface or alarms; providing cylinder location information to staff; ordering replacement cylinders in advance of gas expiry; disablement of cylinders if past their expiry date etc.

It will be appreciated that the second monitoring system (18) is crucial to many aspects of the present invention as it acts as the communicator between devices. In particular, it allows for data from the cylinder, patient and environment to be communicated to the computer (20) and/or any one of a number of other devices and to allow commands, instructions, information and communications to be passed to the cylinders (14). The second monitors (18) may also be used to allow for communication between cylinders (14) and for the passage of user inputted or system generated information between cylinders.

It will also be appreciated that any one or more or all of the computer (20), management system (30), memory (101), further device (60) or human interface (70) may be provided on or in close association with the actual cylinder system (14) such as to be movable therewith. Such an arrangement would give hospital staff immediate access to data and to controlling the supply of gas to the patient. In addition, the management system (30) may be operable to monitor patient specific data (PSD) such as heart rate and/or oxygen saturation and amend the delivery of oxygen to the patient dependent upon pre-defined or specified control requirements (QR's). These control requirements may include any one or more of:

a) Inputting max and/or min oxygen saturation levels to be maintained
b) Monitoring oxygen saturation of the patient
c) Adjusting oxygen delivery depending upon received data on actual oxygen saturation
d) Adjusting the oxygen delivery in accordance with a pre-defined control algorithm and/or
e) Adjusting the oxygen deliver manually.

In Operation

The operation of the above system (10) and cylinder system (14) will now be described with reference to the drawings in general. A cylinder system (14) being filled in a filling station location A will be identified by the second monitoring system (18) by way of an identification signal sent via said first monitoring system (16). The second monitoring system (18) may send command signals to the first monitoring system (16) for causing control over the operation of the cylinder system (14) such as to prevent inadvertent gas delivery whilst within the filling station and/or to automatically close and maintain closed the valve (34) during an adverse event such as a fire or excessive vibration caused by, for example, an earthquake. These control parameters may be applied in any one of the locations A to F detailed in the above and below descriptions. Cylinder specific data (CSD) and/or environment specific data (ESD) is uploaded to the second monitoring system (18A) for further transmission within the overall system (10). Information such as filling date may be used to calculate an expiry date such as to ensure good management of gas safety. Environment specific data (ESD) may be used to control the cylinder valve and/or alarms in the event of an adverse environmental event such as detection of smoke, unexpected temperature variation, adverse vibration etc.

After filling, a cylinder system (14) is usually transported in some manner by means of, for example, a delivery truck (200) which may also be fitted with a second monitoring system (18B). This monitoring system may send signals to first monitoring system (16) of the cylinder system (14) such as to ensure gas may not be dispensed during transit and/or to ensure audio alarms are set to maximum volume and may also be used to place the cylinder system (14) into a sleep mode such as to manage the power demand of said cylinder. Again, environment specific data (ESD) may be used to control the cylinder valve and/or alarms in the event of an adverse environmental event such as detection of smoke, unexpected temperature variation, adverse vibration etc. The systems (16), (18) may also be configured to transmit location information and cylinder specific data (CSD) so as to allow for good cylinder management. Such information may be used to ensure the hospital knows that ordered gas cylinders are in transit and to advise staff what quantity of cylinder systems (14), gas type and cylinder type are being transported. The second monitoring system (18) may communicate it's the location of the cylinder system (14) by means of GPS transmission.

Upon delivery to the store location C, the store monitoring system (18) will identify the cylinders and cylinder specific data (CSD) is uploaded to the second monitor (18C) for onward transmission. Again, the second monitor (18C) may be used to manage any aspect of the cylinder system (14) mentioned herein but, in particular, it may be used to manage the power by placing the cylinders into sleep mode and may prevent gas being delivered by activating an auto-close mode on the cylinder valve (34). Again, environment specific data (ESD) may be used to control the cylinder valve and/or alarms in the event of an adverse environmental event such as detection of smoke, unexpected temperature variation, adverse vibration etc.

Cylinder system (14) may remain in the store C for some time or may then be onward transferred to locations in which gas is expected to be dispensed, such as those shown by way of example as locations D to F. In such locations it will be expected that the cylinders (14) will be required to deliver gas and, consequently, the control over the cylinder valve (34) is amended accordingly such as to allow such delivery. This control may be modified on a time basis such as to prevent delivery of gas during periods where gas would not be expected to be delivered and/or to prevent gas being delivered in the absence of patient specific data (PSD). In the example of location D, the cylinder system (14) is present on a hospital ward D and communicates with the ward specific second management system (18D) such as to transfer cylinder specific information and/or patient specific data (PSD) and/or environment specific data (ESD) to the main computer (20), a further device (60) or a human interface module (70), all of which have been discussed above.

Whilst the cylinder system (14) is at location D, it may be desirable to reduce the volume of any alarms during the night or at any other time and it may also be desirable to ensure that cylinder specific data (CSD) such as gas remaining is elevated in importance such as to ensure the continuity of supply in the event of heavy or unexpected use. In particular, PSD may be transmitted such as to inform staff of patient parameters upon which they may make clinical decisions. The transfer of PSD may also include stored PSD as stored in memory (101). Further information such as gas demand and gas flow may be transmitted such as to allow for the creation of an alarm or control signal in the event that the delivery does not match the demand or the patient is not responding to the gas delivery in the manner that would be expected. Such alarms would allow early investigation and amendment of treatment or modification of gas delivery or investigation and solving of any as delivery problems. Such problems may include the patient lying on the gas delivery supply or the supply being disconnected from the patient. Environment specific data (ESD) may be used to close the cylinder valve (34) upon detection of smoke or any other adverse environment specific data (ESD). Smoke may be detected as a result of the patient having a cigarette, which may have significant safety implications if the gas being delivered is oxygen. ESD may be used to amend the volume of any alarms or alter the control of the cylinder in any other way.

It will be appreciated that the management system (30) may be provided on the cylinder system (14) itself such as to provide a control system (10) immediately available to the medical staff without resorting to a further device. It will also be appreciated that the cylinder system (14) may include a human interface module (70) provided Use in surgery (location E) may require the audio alarms to be disabled or amended so as not to interfere with other alarms and the system (10) may be used to cause PSD to be transmitted to the computer (20) or sharing with other members of staff outside of the operating theatre or to further device (60) or a human interface module (70) for sharing in another way.

Use at home (location F) may require the human interface (70) to be caused to display simple instructions to the patient P so as to allow the self solution of technical or medical problems. In addition, the audio alarms may be increased in volume and any manual overrides may be disabled.

The above system (10) may also be used to broadcast or transfer information or commands or alarms between cylinder systems (14) or to cylinder systems (14). For example, as each cylinder system (14) includes an alarm and each cylinder system (14) is connected to the system (10), the system may be used to cause an evacuation alarm to be transmitted to each cylinder system (14) so as to allow staff to respond accordingly. In addition, instructions may be sent to a home patient at location (F). It will be appreciated that any form of data or commands may be transmitted to or from cylinders (14) at any one or more of locations (A-F) and that modifications, deletion and variations to the data being transferred, alarms being created or modified and controls being implemented is possible. The above specific examples are, therefore, illustrative only.

It will be appreciated that the above cylinder system (14) is mobile and may be independent of a hospital gas supply system whilst still being able to monitor PSD and CSD and using this data to control or modify or prevent the delivery of gas to a patient. This is in stark contrast with the prior art of GB 2508897 discloses a wall mounted gas control system for controlling the delivery of oxygen to a patient in which some patient specific data such as oxygen saturation is monitored and the system is only operable to control the delivery of oxygen to the patient dependent upon received patient data and programmed inputs such as target oxygen saturation. The system also provides some alarms which are generated when adverse events, such as non-receipt of patient oxygen saturation data, occur such as to warn the hospital staff or patient that something is wrong.

The provision of ESD in the present invention allows for a still higher degree of safety control to be applied to the delivery of gas to patients.

The invention claimed is:

1. A control system for managing the supply of bottled gas to users, the system comprising:
   a) a plurality of gas cylinder systems having a gas cylinder for receiving and distributing gas contained therein;
   b) a first electronic monitoring system associated with said gas cylinder system and operable to monitor parameters associated with said cylinder system;
   c) a plurality of second monitoring systems associated with one or more locations in which said cylinder may reside and being operable to monitor the presence or absence of any of said cylinder systems within said one or more locations, wherein said first monitoring system includes an operable mode in which it is fully operational and a sleep mode in which it is not fully operable but is able to be placed back into the operable mode upon receipt of a signal from said plurality of second monitoring systems and wherein said plurality of second monitoring systems are operable to send a signal to said first monitoring system to cause said first monitoring system to adopt said operable mode or said sleep mode as and when required; and
   d) a computer system in communication with each of said second monitoring systems for receiving information therefrom relating to the presence or absence of said cylinder system in said one or more locations.

2. The system according to claim 1, wherein said first monitoring system is configured for monitoring one or more of cylinder specific data relating to any one or more of: cylinder identification, gas supply time remaining, expiry date, cylinder type, cylinder location, environmental temperature, gas usage, time since filling, rate of gas usage, internal cylinder gas pressure, internal cylinder gas temperature, usage data, transportation data or gas remaining.

3. The system according to claim 1, further comprising a patient monitor for monitoring patient specific data, the patient monitor configured to monitor one or more of the following patient specific data: patient identity, patient type, blood pressure, heart rate, oxygen saturation, breathing and gas usage, and wherein said patient monitor is connected to said first monitoring system for transmitting patient specific data to said first monitoring system.

4. The system according to claim 1, further comprising an environment monitor for monitoring environment specific data and configured to monitor one or more of the following environment specific data: location, smoke, temperature, movement or vibration.

5. The system according to claim 4, further comprising a GPS location device associated with said cylinder for broadcasting the geographical location of said cylinder.

6. The system according to claim 1, wherein said first electronic monitoring system includes a transmitter for transmitting data to said second monitoring system, a further device or a human interface module.

7. The system according to claim 1, wherein said second monitoring system includes a transmitter for transmitting data to said computer system, a further device or a human interface module.

8. The system according to claim 1, wherein said first electronic monitoring system includes a receiver for receiving information or commands from said second monitoring system, a further device or a human interface module.

9. The system according to claim 1, wherein said second electronic monitoring system includes a receiver for receiving information or commands from said computer system, a further device or a human interface module.

10. The system according to claim 1, wherein said computer includes a management system for receiving monitored data.

11. The system according to claim 10, wherein said management system includes a command module for causing operational commands to be transmitted to said first monitoring system dependent upon monitored data received thereby.

12. The system, according to claim 1, wherein said cylinder system includes a controllable outlet valve for controlling the gas output from said cylinder system and wherein said first monitoring system includes a controller, said outlet valve is operably linked to said controller for being controlled thereby and wherein said valve is controllable to alter or prevent the flow of gas from said cylinder system dependent upon commands received from said second monitoring system, said further device or a human interface module.

13. The system according to claim 12, further comprising programmed one or more automatic valve closure commands for being transmitted to said first monitoring system upon receipt of an adverse situation signal generated by detection of any one or more of: smoke, adverse vibration, adverse movement, adverse temperature, excessive or non-programmed gas usage, excessive or unexpected gas pressure, gas dispensing in the absence of receipt of patient specific data, passage of an expiry date, unexpected or non-programmed location of cylinder system, absence of a command signal from said computer system, a further device or a human interface module.

14. The system according to claim 13, further comprising an automatic check and restart function for periodically checking received data after valve closure due to detection of an adverse situation signal and re-starting gas flow in the absence of receipt of a further adverse situation signal.

15. The system according to claim 14, wherein said automatic check and restart function includes an intelligent restart function for allowing gas to be delivered in accordance with a pre-determined control strategy.

16. The system according to claim 1, further comprising a human interface module for providing information or warnings to a user or accepting cylinder operational command inputs from a user and wherein said human interface module has multiple modes of operation and wherein said first monitoring system is operable to alter the mode of operation of the interface module dependent upon an inputted signal from said second monitoring system.

17. The system according to claim 16, wherein said human interface module is operable to change or cancel any one or more of audio output, visual output, operational command output, user access capability, user interface capability or operational capability.

18. The system according to claim 16, wherein said human interface module is operable to receive patient specific data including patient identification or patient type information.

19. The system according to claim 1, further comprising a wireless communication system between said first monitoring system and said second monitoring system.

20. The system according to claim 1, further comprising a wireless communication system between said second monitoring system and said computer system.

21. The system according to claim 1, wherein said computer system comprises a cloud based computer system.

22. The system according to claim 1, wherein said computer system comprises a mainframe computer system.

23. The system according to claim 1 further comprising a memory for storing any one or more of patient specific data, cylinder specific data environment, or specific data.

\* \* \* \* \*